(12) United States Patent
Kim et al.

(10) Patent No.: US 7,883,510 B2
(45) Date of Patent: Feb. 8, 2011

(54) VERTEBRAL STAPLES AND INSERTION TOOLS

(75) Inventors: Daniel Huan Kim, Mountain View, CA (US); Michael Carl Michielli, Medway, MA (US); Amie Borgstrom, North Attleborough, MA (US)

(73) Assignee: DePuy Spine, Inc., Raynham, MA (US)

( * ) Notice: Subject to any disclaimer, the term of this patent is extended or adjusted under 35 U.S.C. 154(b) by 1133 days.

(21) Appl. No.: 10/927,779

(22) Filed: Aug. 27, 2004

(65) Prior Publication Data

US 2007/0191850 A1 Aug. 16, 2007

(51) Int. Cl.
*A61B 17/064* (2006.01)
(52) U.S. Cl. ........................................ 606/75
(58) Field of Classification Search ............. 606/69–72, 606/75, 280, 281, 286, 293, 325, 329; 623/13.14
See application file for complete search history.

(56) References Cited

U.S. PATENT DOCUMENTS

| | | | |
|---|---|---|---|
| 4,263,903 A | | 4/1981 | Griggs |
| 4,960,420 A | * | 10/1990 | Goble et al. ............ 606/72 |
| 5,314,427 A | * | 5/1994 | Goble et al. ............ 606/72 |
| 5,395,372 A | | 3/1995 | Holt et al. |
| 5,454,814 A | * | 10/1995 | Comte ..................... 606/75 |
| 5,487,741 A | * | 1/1996 | Maruyama et al. ...... 606/60 |
| 5,601,558 A | | 2/1997 | Torrie et al. |
| 5,616,144 A | | 4/1997 | Yapp et al. |
| 5,662,655 A | * | 9/1997 | Laboureau et al. ...... 606/75 |
| 5,779,707 A | | 7/1998 | Bertholet et al. |
| 5,925,047 A | | 7/1999 | Errico et al. |
| 5,947,969 A | | 9/1999 | Errico et al. |
| 5,960,629 A | * | 10/1999 | McClain et al. ......... 60/547.2 |
| 6,013,077 A | * | 1/2000 | Harwin .................. 606/232 |
| 6,136,001 A | | 10/2000 | Michelson |
| 6,336,928 B1 | | 1/2002 | Guerin et al. |
| 6,524,311 B2 | | 2/2003 | Gaines, Jr. |
| 6,533,787 B1 | | 3/2003 | Lenke et al. |
| 6,635,062 B2 | | 10/2003 | Ray, III et al. |
| 6,692,503 B2 | | 2/2004 | Foley et al. |
| 7,314,591 B2 | * | 1/2008 | Priedeman, Jr. ......... 264/308 |

(Continued)

FOREIGN PATENT DOCUMENTS

EP          0358372          3/1990

(Continued)

*Primary Examiner*—Thomas C Barrett
*Assistant Examiner*—Michael J Araj
(74) *Attorney, Agent, or Firm*—Nutter McClennen & Fish LLP

(57) ABSTRACT

Implantable vertebral staples and tools for use with the same are provided. In general, an exemplary vertebral staple according to the present invention includes a staple body having at least one long spike formed thereon for allowing rotation of the body when the long spike is partially inserted in bone. The staple body can also include one or more short spikes formed thereon and adapted to prevent rotation of the body when the long and short spikes are fully inserted into bone. The present invention also provides an inserter tool that can be used to implant the vertebral staple, and also a drill guide that can be used, preferably in combination with the inserter tool, to drill holes through the bone in alignment with one or more holes formed in the vertebral staple.

12 Claims, 7 Drawing Sheets

U.S. PATENT DOCUMENTS

| | | | |
|---|---|---|---|
| 7,481,830 B2 * | 1/2009 | Wall et al. | 606/297 |
| 2002/0095155 A1 | 7/2002 | Michelson | |
| 2002/0099378 A1 | 7/2002 | Michelson | |
| 2002/0173790 A1 | 11/2002 | Chang et al. | |
| 2002/0193795 A1 * | 12/2002 | Gertzbein et al. | 606/61 |
| 2004/0073222 A1 | 4/2004 | Koseki | |

FOREIGN PATENT DOCUMENTS

| | | |
|---|---|---|
| EP | 1402829 | 3/2004 |
| WO | 01/03570 | 1/2001 |
| WO | WO 02/30307 | 4/2002 |

* cited by examiner

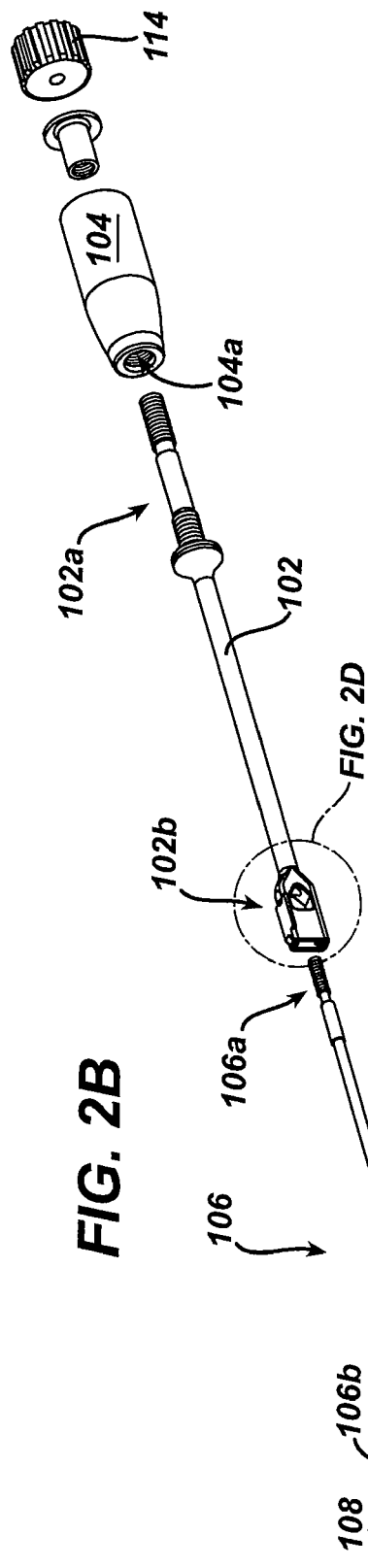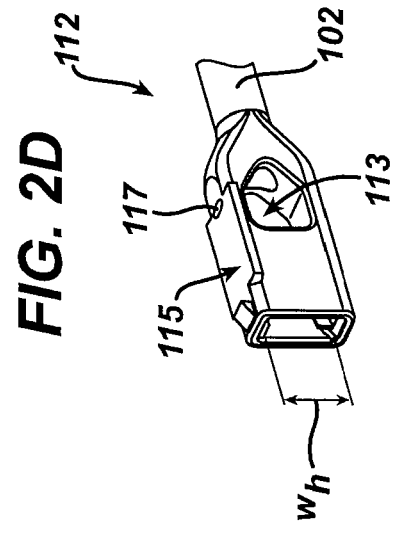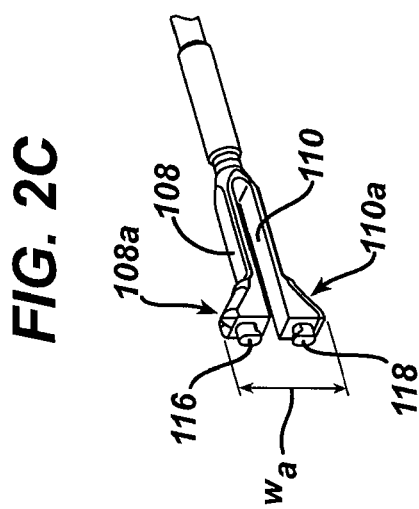

VERTEBRAL STAPLES AND INSERTION TOOLS

FIELD OF THE INVENTION

The present invention relates to spinal implants, and in particular to vertebral staples and tools for implanting the same.

BACKGROUND OF THE INVENTION

Spinal fixation devices are used in orthopedic surgery to align and/or fix a desired relationship between adjacent vertebral bodies. Such devices typically include a spinal fixation element, such as a relatively rigid fixation rod, that is coupled to adjacent vertebrae by attaching the element to various anchoring devices, such as hooks, bolts, wires, or screws. Alternatively, two rods can be disposed on the lateral or anterior surface of the vertebral body in a substantially parallel relationship. The fixation rods can have a predetermined contour that has been designed according to the properties of the target implantation site, and once installed, the rods hold the vertebrae in a desired spatial relationship, either until desired healing or spinal fusion has taken place, or for some longer period of time.

Several plate and screw systems have been designed for instrumentation of the spinal column. A typical construct utilizes vertebral staples, spinal screws and locking nuts, and two spinal fixation rods. A staple is implanted in each adjacent vertebra and two screws are inserted through holes formed in the staple such that the screw heads rest against the staple. The spinal fixation rods are then positioned within the screw heads such that the rods are substantially parallel to one another and they span across multiple adjacent vertebrae. The rods are then locked in place using the locking nuts, thereby maintaining the vertebrae in a fixed position.

Most vertebral staples are used to impair toggling action by the screws implanted therethrough, and they are intended to prevent motion which can cause the screw to bone interface from breaking down. Each vertebral staple typically includes two or more spikes, often placed on each corner of the staple, to secure the staple to a vertebra. The staple is implanted in the vertebra by positioning it against the vertebra and applying a force thereto to impact the staple into the bone.

While current vertebral staples are effective, one drawback is that they do not allow the position of the staple to be adjusted once the staple is implanted in the vertebra. If the staple is not properly aligned, the surgeon is required to remove the staple and re-position it. One other draw back of current vertebral staple designs is that they can be difficult to manipulate using existing insertion tools. In particular, most vertebral staples are not planar, but rather they have uneven surfaces. As a result, it can be difficult to grasp the staple using an insertion tool, and to evenly impact the staple into the vertebra.

Accordingly, there remains a need for an improved vertebral staple that includes features which allow the position of the staple with respect to the vertebra to be adjusted prior to fully implanting the staple. There also remains a need for improved methods and devices for grasping and implanting a vertebral staple.

SUMMARY OF THE INVENTION

The present invention provides implantable vertebral staples and tools for use with the same. In one embodiment, an implantable vertebral staple is provided and it includes a staple body having superior and inferior surfaces and at least two holes extending therethrough, at least one perimeter spike formed on the inferior surface of the staple body, and a central spike preferably formed at a substantial mid-portion of the inferior surface of the staple body. The staple body can have a variety of shapes and sizes, but preferably it has a shape that is adapted to match the contour of an anterior surface of a vertebral body. More preferably, the staple body includes superior and inferior ends with a longitudinal axis extending therebetween, and the staple body is curved about a transverse axis that intersects the longitudinal axis. The staple body can also include two holes formed in substantially diagonally opposed corners of the body opposite to the first and second perimeter spikes.

The spikes formed on the staple body can also have a variety of configurations. In one exemplary embodiment, the central spike has a length that is greater than a length of the perimeter spike(s), and more preferably the difference between the length of the central spike and the length of the perimeter spike(s) is in the range of about 2 mm to 5 mm. The staple body also preferably includes first and second perimeter spikes. While the perimeter spikes can be formed anywhere on the body, in one embodiment the staple body is substantially rectangular in shape and the first and second perimeter spikes are formed adjacent to substantially diagonally opposed corners of the body.

In another embodiment, the staple body can include first and second bores formed therethrough for mating with an insertion tool. The first and second bores are preferably formed on opposed sides of the central spike. The plate can also include a mid-portion that is substantially planar, and the first and second bores can be formed in the mid-portion.

In yet another embodiment, an implantable vertebral staple is provided having a staple body with opposed thru-holes formed therein, a long spike, and at least one short spike. The short spike(s) is adapted to allow rotation of the body when the long spike is partially inserted in bone, and it is adapted to prevent rotation of the body when the long and short spike(s) are fully inserted into bone.

The present invention also provides a spinal implant kit that includes a vertebral staple having a plurality of spikes formed thereon and adapted to be implanted in bone, and an inserter tool that is adapted to removably engage the vertebral staple. At least one of the spikes on the staple preferably has a length that is greater than a length of the remaining spikes such that the vertebral staple is freely rotatable when the vertebral staple is partially inserted into bone. In an exemplary embodiment, the inserter tool includes a staple-engaging member that is adapted to removably engage the staple. More preferably, the staple-engaging member has first and second opposed grasping arms that are movable between an extended position and a retracted in which the arms are effective to engage the staple. The arms can optionally be biased to the extended position and they can be moved toward one another in the retracted position. Each arm can optionally include a hook-member formed on a distal end thereof and adapted to engage the staple. The present invention also provides a drill guide that is removably matable to the inserter tool such that at least one lumen extending through the drill guide is aligned with at least one hole formed in the staple.

In other aspects of the invention, an inserter tool for use with a vertebral staple is provided having an elongate shaft with a proximal handle and a distal end, and a staple-engaging member that is coupled to the elongate shaft and that is movable between an extended position and a retracted position in which the opposed grasping arms are adapted to engage the vertebral staple. In an exemplary embodiment, the staple-engaging member extends through an inner lumen extending through the elongate shaft, and the distal end of the elongate shaft includes a housing that is adapted to receive at least a portion of the grasping arms on the staple-engaging member. The inserter tool can also include an actuating mechanism formed therein and adapted to move the staple-engaging member between the retracted and extended positions. The actuating mechanism can be, for example, a rotatable member that is mated to the staple-engaging member.

The inserter tool can also optionally include a drill guide that is removably matable to the elongate shaft and that has at least one lumen extending therethrough for receiving a tool. In an exemplary embodiment, the drill guide includes a cavity formed therein for receiving the housing. The drill guide and/or the housing can also optionally include a mating element formed thereon to allow the components to be removably mated to one another. In one exemplary embodiment, the mating element is a T-shaped member formed on the housing and a corresponding T-slot formed within the guide for removably receiving the T-shaped member on the housing of the inserter tool.

The present invention also provides a method for implanting a spinal staple that includes the steps of partially inserting a long spike formed on a staple into a vertebra, rotating the staple about the long spike to position at least one hole formed in the staple relative to the vertebra, and fully inserting the central spike into the vertebra such that one or more short spikes on the staple extend into the vertebra to prevent rotation of the staple relative to the vertebra. An inserter tool can optionally be used to facilitate insertion of the staple into a vertebra.

BRIEF DESCRIPTION OF THE DRAWINGS

The invention will be more fully understood from the following detailed description taken in conjunction with the accompanying drawings, in which:

FIG. 2B is a disassembled perspective view of the inserter tool shown in FIG. 2A;

FIG. 2C is an enlarged view of the staple-grasping portion of the inserter tool shown in FIG. 2B;

FIG. 2D is an enlarged view of the distal portion of the elongate shaft of the inserter tool shown in FIG. 2B;

DETAILED DESCRIPTION OF THE INVENTION

Figure 1A:
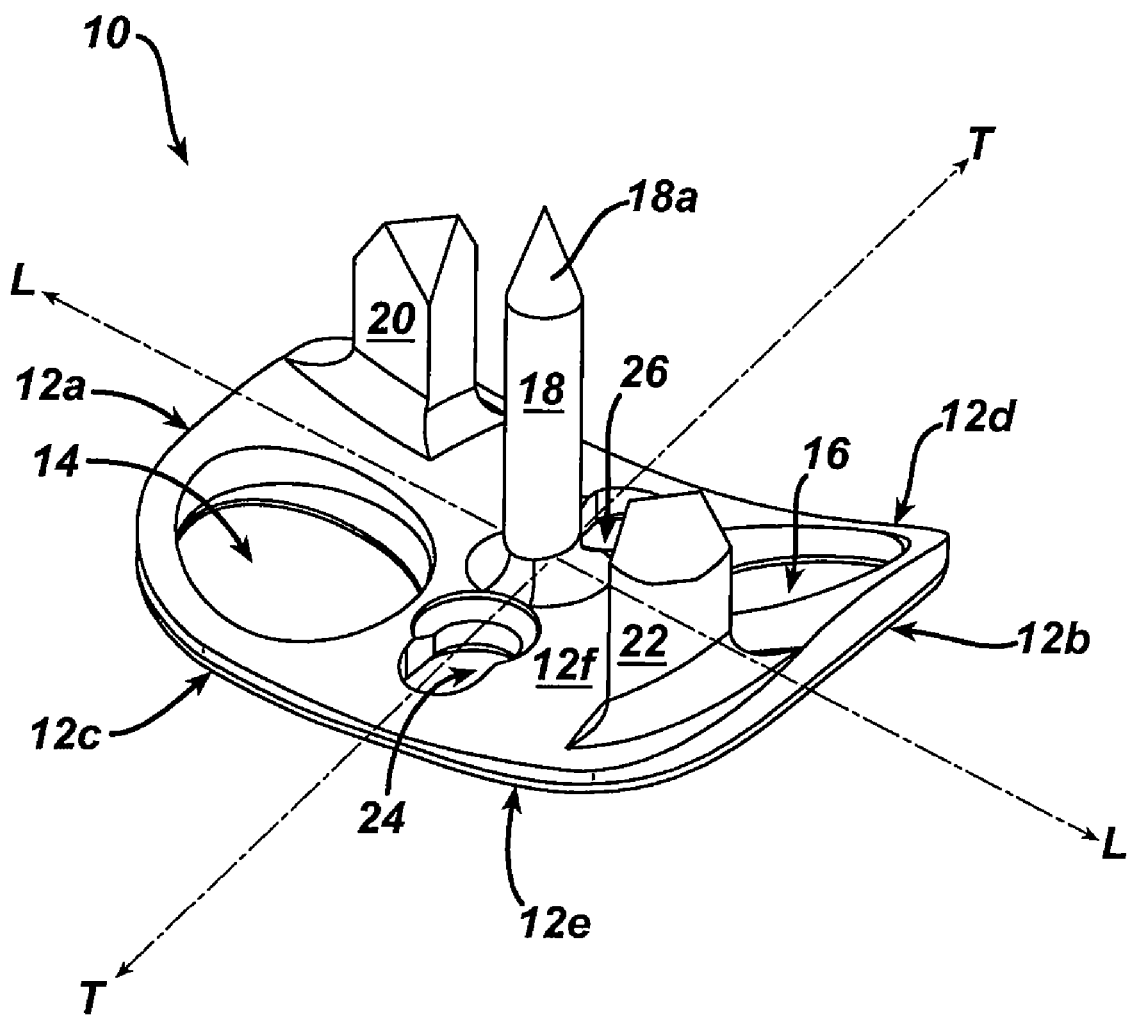
FIG. 1A is an inferior perspective view of a vertebral staple according to one exemplary embodiment of the present invention.

The present invention provides implantable vertebral staples and tools for use with the same. In general, an exemplary vertebral staple according to the present invention includes a staple body having at least one long spike formed thereon for allowing rotation of the body when the long spike is partially inserted in bone. The staple body can also include one or more short spikes formed thereon and adapted to prevent rotation of the body when the long and short spikes are fully inserted into bone. The present invention also provides an inserter tool that can be used to implant a vertebral staple, and also a drill guide that can be used, preferably in combination with the inserter tool, to guide tools through one or more holes formed in a vertebral staple.

FIGS. 1A-1D illustrate one exemplary embodiment of a vertebral staple 10. As shown, the staple 10 includes a staple body 12 having opposed first and second ends 12a, 12b, opposed transverse sides 12c, 12d, and opposed superior and inferior surfaces 12e, 12f. The shape, size, and configuration of the body 12 can vary depending on the intended use, but preferably the body 12, or at least the inferior surface 12f of the body 12, has a shape and size that is adapted to be positioned against a vertebra in a patient's spine. In an exemplary embodiment, as shown, the body 12 is curved about a transverse axis T that extends between the opposed transverse sides 12c, 12d, and that extends in a direction that is substantially perpendicular to a longitudinal axis L extending between the opposed first and second ends 12a, 12b of the body 12. The curvature is preferably adapted to conform to the shape of a surface of a vertebral body, such as an anterior surface, preferably for use in an anterior surgical approach. In some embodiment, the curvature can be adapted to conform to the shape of a lateral face of a vertebral body for use in an anterio-lateral approach. A person skilled in the art will appreciate that the body 12 can have virtually any shape and size, and that the shape and size can vary depending on the intended implant location.

The body 12 of the vertebral staple 10 can also include one or more thru-holes formed therein for receiving spinal screws or other spinal implants. In the illustrated embodiment, two holes 14, 16 are formed in diagonally opposed corners of the body 12 such that the first hole 14 is formed adjacent to the first end 12a and the first transverse side 12c and the second hold 16 is formed adjacent to the second end 12b and the second transverse side 12d. A person skilled in the art will appreciate that the number of holes as well as the position of the holes can vary. The shape and size of the thru-holes can also vary and the holes can include features known in the art to facilitate insertion of a spinal screw or other implant therethrough.

The body 12 of the staple 10 can also include one or more spikes formed on the inferior surface 12f thereof and adapted to extend into bone to affix the staple 10 to the bone. In an exemplary embodiment, at least one of the spikes is configured to allow the body 12 to rotate freely when the spike is partially inserted into bone. Once the staple is properly positioned, the spike can be fully inserted into bone, thereby causing one or more additional spikes on the body 12 to extend into the bone to prevent rotation of the staple 10.

Figure 1B:
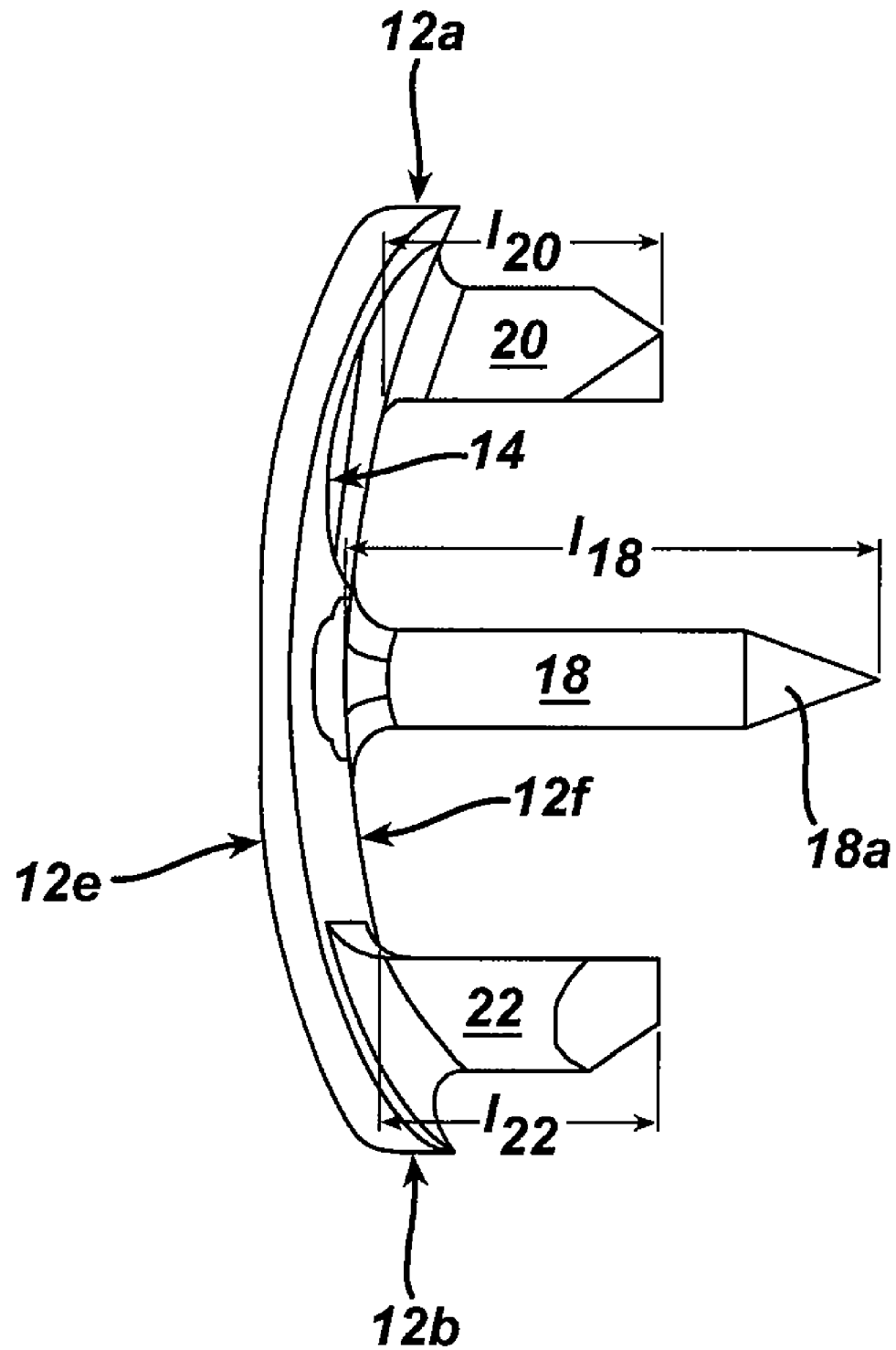
FIG. 1B is a side view of the vertebral staple shown in FIG. 1A.
Figure 1C:
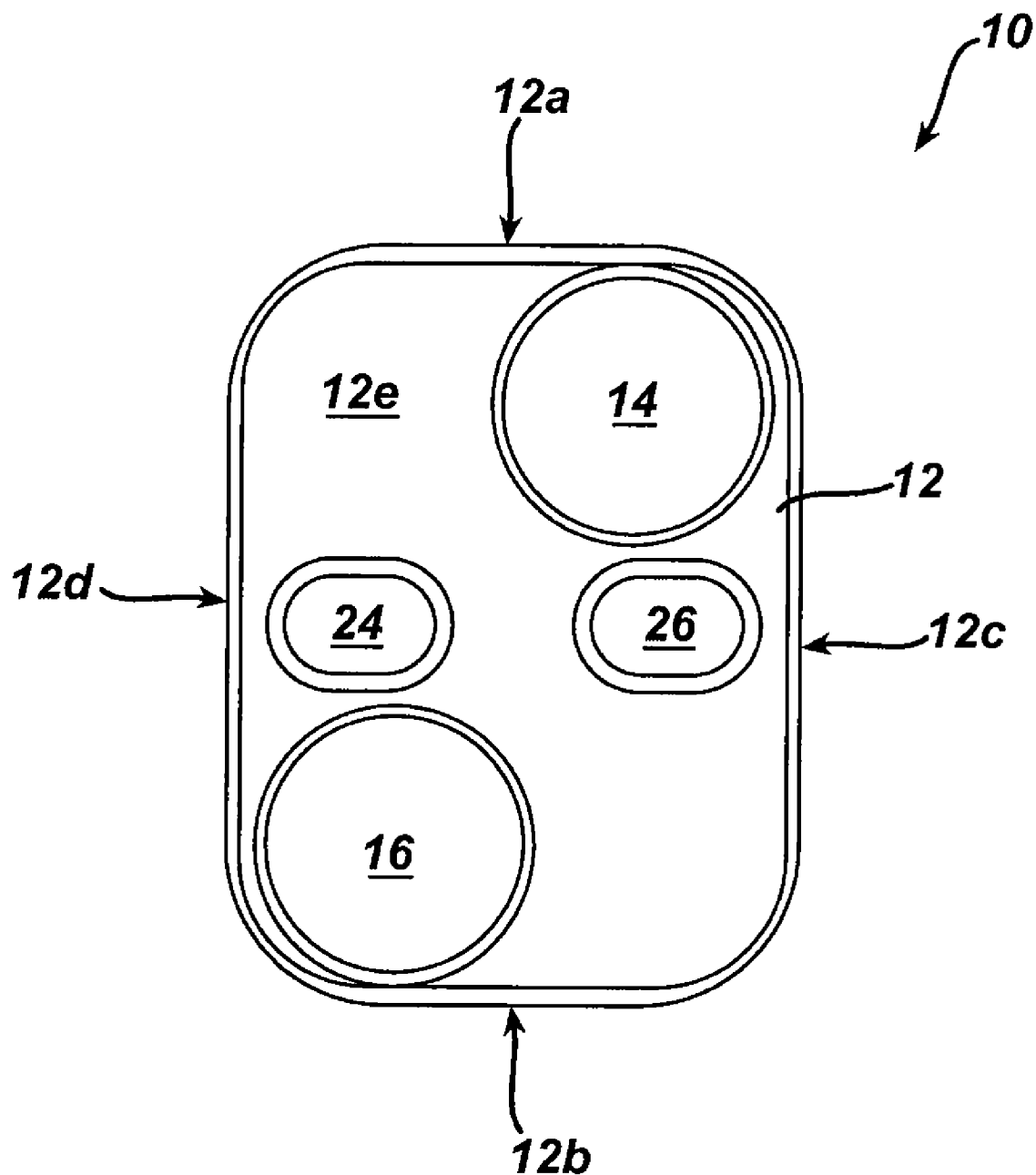
FIG. 1C is a superior view of the vertebral staple shown in FIG. 1A.

As shown in FIGS. 1A and 1B, the body 12 includes a central spike 18 formed at a substantial mid-portion thereof, and one more additional spikes, and preferably two additional spikes referred to as the first and second perimeter spikes 20, 22, formed adjacent to the ends 12a, 12b and sides 12c, 12d of the body 12. The central spike 18 preferably has a length $l_{18}$ that is greater than a length $l_{20}$, $l_{22}$ of the first and second perimeter spikes 20, 22. Such a configuration allows the central spike 18 to be inserted in bone to allow the body 12 to rotate thereabout without interference from the perimeter spikes 20, 22. The difference in length $l_{18}$, $l_{20}$, $l_{22}$ between the central spike 18 and the perimeter spikes 20, 22 should thus be sufficient to allow at least a portion of the central spike 18 to be inserted into bone without the perimeter spikes 20, 22 coming into contact with the bone. While the length $l_{18}$, $l_{20}$, $l_{22}$ of each spike 18, 20, 22 can vary, in an exemplary embodiment the difference between the length $l_{18}$ of the central spike 18 and the length $l_{20}$, $l_{20}$ of each perimeter spike 20, 22 is in the range of about 2 mm to 5 mm. This difference preferably remains the same for surgical staples 10 have various sizes and various spike lengths.

The location of each spike 18, 20, 22 can also vary. In particular, while central spike 18 is shown at a substantial center-point of the body 12, the spike 18 can be positioned anywhere on the body 12. Likewise, the perimeter spikes 20, 22 can also be formed anywhere on the body 12. In the illustrated embodiment, the perimeter spikes 20, 22 are formed in diagonally opposed corners of the body 12 such that the first perimeter spike 20 is positioned adjacent the first end 12a and the second side 12d, and the second perimeter spike 22 is positioned adjacent the second end 12b and the first side 12c. The perimeter spikes 20, 22 are also positioned on opposed sides of the longitudinal and transverse axes L, T relative to the thru-holes 14, 16 formed in the body 12.

The shape of each spike 18, 20, 22 can also vary, but the spikes 18, 20, 22 should be adapted to extend into bone. In an exemplary embodiment, the central spike 18 has a generally elongate cylindrical shape with a pointed distal tip 18a that is configured to penetrate into bone. The cylindrical shape facilitates rotation of the body 12 about the central spike 18. The perimeter spikes 20, 22 can also have a substantially cylindrical shape, but as shown in FIGS. 1A and 1B, the perimeter spikes 20, 22 have a substantially triangular-shaped cross-section such that each spike 20, 22 includes three sides extending there along. The spikes 20, 22 can also include a beveled tip 20a, 22a, as shown, to facilitate penetration of the spikes 20, 22 into bone.

As indicated above, a person skilled in the art will appreciate that the location, quantity, shape, and size of the spikes on the body 12 can vary depending on the intended use, as well as the shape and size of the body 12 itself. The drawings are merely illustrative of an exemplary embodiment of a vertebral staple 10.

In use, the staple 10 can be positioned at a desired implant site, preferably adjacent to a vertebral body, and a force can be applied to the body 12 to at least partially impact the central spike 18 into the vertebra. The staple 10 can then be rotated to position the thru-holes 14, 16 in the body 12 at a desired location for screw placement therethrough, and once properly positioned an additional force can be applied to the body 12 to fully impact the central spike 18 into the vertebra, thereby impacting the perimeter spikes 20, 22 into the vertebra. As a result, the perimeter spikes 20, 22 will prevent the body 12 from rotating with respect to the vertebra, thereby securely implanting the surgical staple 10. The vertebral staple 10 can thereafter be used to protect the vertebra, provide enhanced stability, and/or to prevent pullout of one or more spinal screws or other spinal implants inserted through the one or more thru-holes 14, 16 formed in the body 12.

The present invention also provides an inserter tool 100, shown in FIGS. 2A-2D, that can be used to manipulate and implant the vertebral staple 10. While the inserter tool 100 can have various configurations, it is preferably adapted to grasp and removably engage a portion of a staple such that the tool 100 can be used to position the staple against bone. The tool 100 can also receive the force that is necessary to impact the staple into bone, and it can optionally include features to facilitate preparation of the bone for receipt of one or more spinal screws or other implants.

Figure 2A:
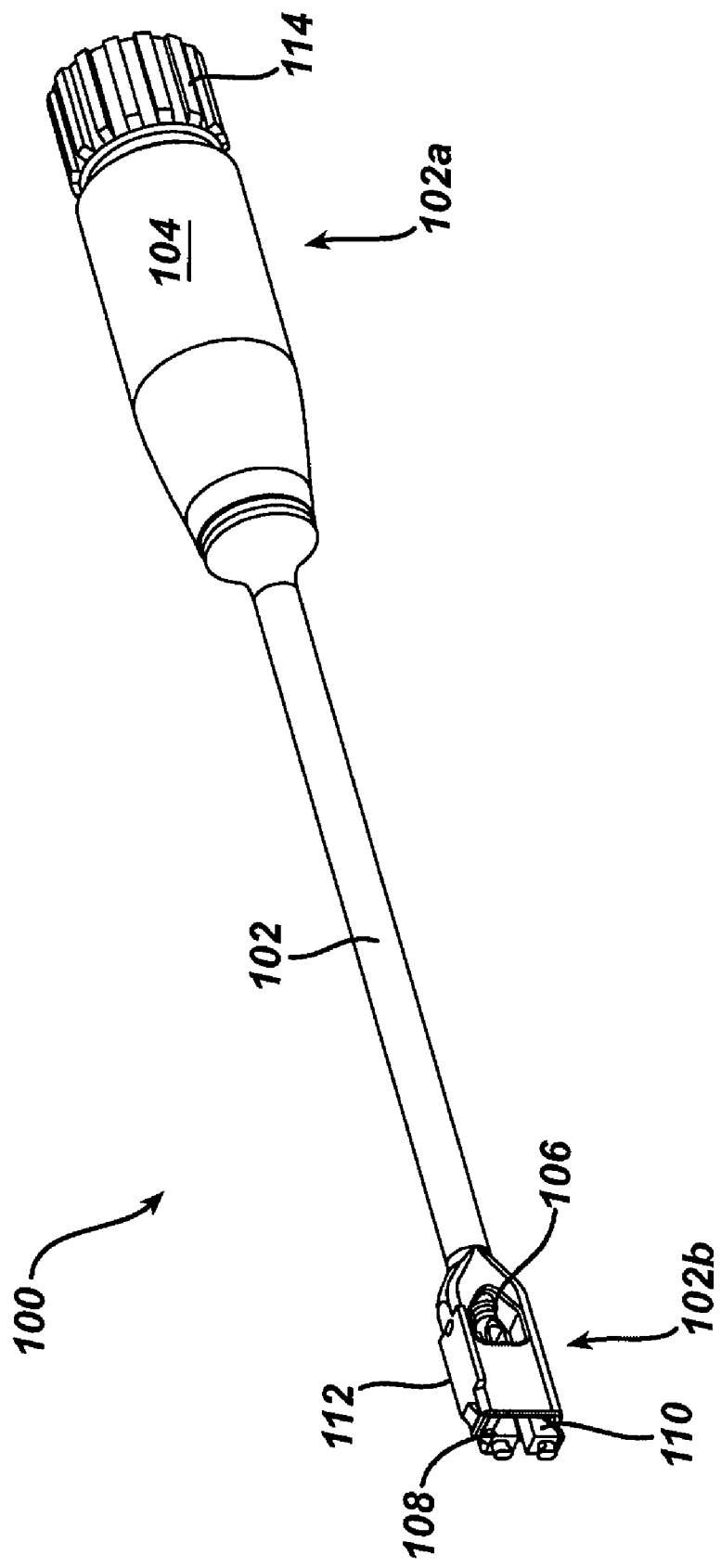
FIG. 2A is a perspective view of one embodiment of an inserter tool for use with a vertebral staple.

In the embodiment shown in FIGS. 2A-2D, the inserter tool 100 generally includes an elongate shaft 102 having a proximal end 102a and a distal end 102b. The proximal end 102a can include a handle 104 formed thereon or mated thereto, and the distal end 102b is preferably effective to grasp and removably engage a vertebral staple, such as staple 10 shown in FIGS. 1A-1C. In an exemplary embodiment, a staple-engaging member 106 (FIG. 2B) is disposed through a lumen in the elongate shaft 102 and it is movable between an extended position in which opposed grasping arms 108, 110 formed on the staple-engaging member 106 extend from the distal end 102b of the elongate shaft 102, and a retracted position, as shown in FIG. 2A, in which the opposed grasping arms 108, 110 are at least partially retracted into the elongate shaft 102 and they are adapted to engage a vertebral staple. The inserter tool 100 can also include an actuating mechanism, such as rotating knob 114, that is effective to move the staple-engaging member 106 between the extended and retracted positions, thereby allowing the staple-engaging member 106 to selectively grasp and release a staple.

The elongate shaft 102 can have a variety of shapes of sizes, but, as noted above, it preferably includes a handle 104 that is formed on or mated to a proximal end 102a thereof. In the embodiment shown in FIG. 2B, the handle 104 is threadably matable to the shaft 102 and it is effective to allow a user to grasp and manipulate the tool 100. The handle 104 also includes a lumen extending therethrough for receiving a proximal end 106a of the staple-engaging member 106 to allow the staple-engaging member 106 to couple to an actuating mechanism, as will be discussed in more detail below.

The distal end 102b of the elongate shaft 102 preferably includes a housing 112, shown in more detail in FIG. 2D, that is effective to receive the opposed grasping arms 108, 110 of the staple-engaging member 106. The housing 112 can have virtually any shape and size, but it should be adapted to receive the opposed grasping arms 108, 110 and to cause the arms 108, 110 to move toward one another to engage a vertebral staple. The housing 112 can also be configured to mate with a drill guide, which will be discussed in more detail below with respect to FIG. 3. Moreover, the housing 112 can include features such as a window 113 formed therein to facilitate visual access to a vertebral staple mated to the inserter tool 100.

The staple-engaging member 106 can also have a variety of configurations, but in an exemplary embodiment it is in the form of an elongate shaft having a proximal end 106a that is configured to mate to an actuating mechanism, such as rotatable knob 114, and a distal end 106b that is configured to engage a staple. As indicated above, the distal end 106b can include first and second opposed arms 108, 110 for grasping a staple. The arms 108, 110 can vary in shape and size, but they are preferably effective to move toward one another when the staple-engaging member 106 is retracted into the housing 112 formed on the distal end of the elongate shaft 102, and they are effective to move apart from one another to engage a staple when the staple-engaging member 106 is extended from the housing 112 formed on the distal end of the elongate shaft 102. As shown in detail in FIG. 2C, the arms 108, 110 can be spaced a distance apart from one another in their original state, and they can each include an enlarged or angled portion 108a, 110a formed on an end thereof. In other words, the arms 108, 110 increase in width in a distal direction. The angled portion 108a, 110a allows the arms 108, 110 to be moved toward one another when the angled portion 108a, 110a is retracted into the housing 112, as the housing 112 will preferably have an inner width $w_h$ that is less than a width $w_a$ of the angled portions 108a, 110a. When the staple-engaging member 106 is returned to the extended state, the arms 108, 110 will preferably return to their original spaced-apart condition, shown in FIG. 2C. The arms 108, 110 can optionally be biased to the open, extended position such that the housing 112 applies a force to the arms 108, 110 sufficient to overcome the biasing force when the arms 108, 110 are retracted into the housing.

Each arm 108, 110 can also include an engagement mechanism formed thereon for engaging a vertebral staple. As shown in FIG. 2C, each arm 108, 110 includes a hook 116, 118 formed on a distal-most end thereof. The hooks 116, 118 are preferably adapted to extend into corresponding bores formed in a vertebral staple to engage the staple. Preferably, the hooks 116, 118 extend toward one another such that, when the staple-engaging member 106 is in the extended position and the arms 108, 110 are spaced apart, the hooks 116, 118 can be inserted through adjacent bores formed in a vertebral staple, or they can be positioned adjacent opposed edges of a staple. Conversely, when the arms 108, 110 are moved to the retracted position, the hooks 116, 118 move toward one another to engage the staple. A person skilled in the art will appreciate that the hooks 116, 118 can extend away from one another such that the arms 108, 110 are effective to engage a staple when the arms are in the extended position. Moreover, a variety of other techniques can be used to engage the staple, including a sliding connection, a threaded connection, etc.

As noted above, the inserter tool 100 can also include an actuating mechanism that is effective to move the staple-engaging member 106 between the extended and retracted positions. While various actuating mechanisms can be used, in an exemplary embodiment a knob 114 is threadably mated to a distal end 106a of the staple-engaging member 106 such that rotation of the knob 114 in a first direction is effective to move the staple-engaging member 106 proximally with respect to the elongate shaft 102 into the retracted position, and rotation of the knob 114 in a second opposite direction is effective to move the staple-engaging member 106 distally with respect to the elongate shaft 102 into the extended position. A person skilled in the art will appreciate that a variety of techniques can be used to move the staple-engaging member 106 between the extended and retracted positions.

Figure 3:
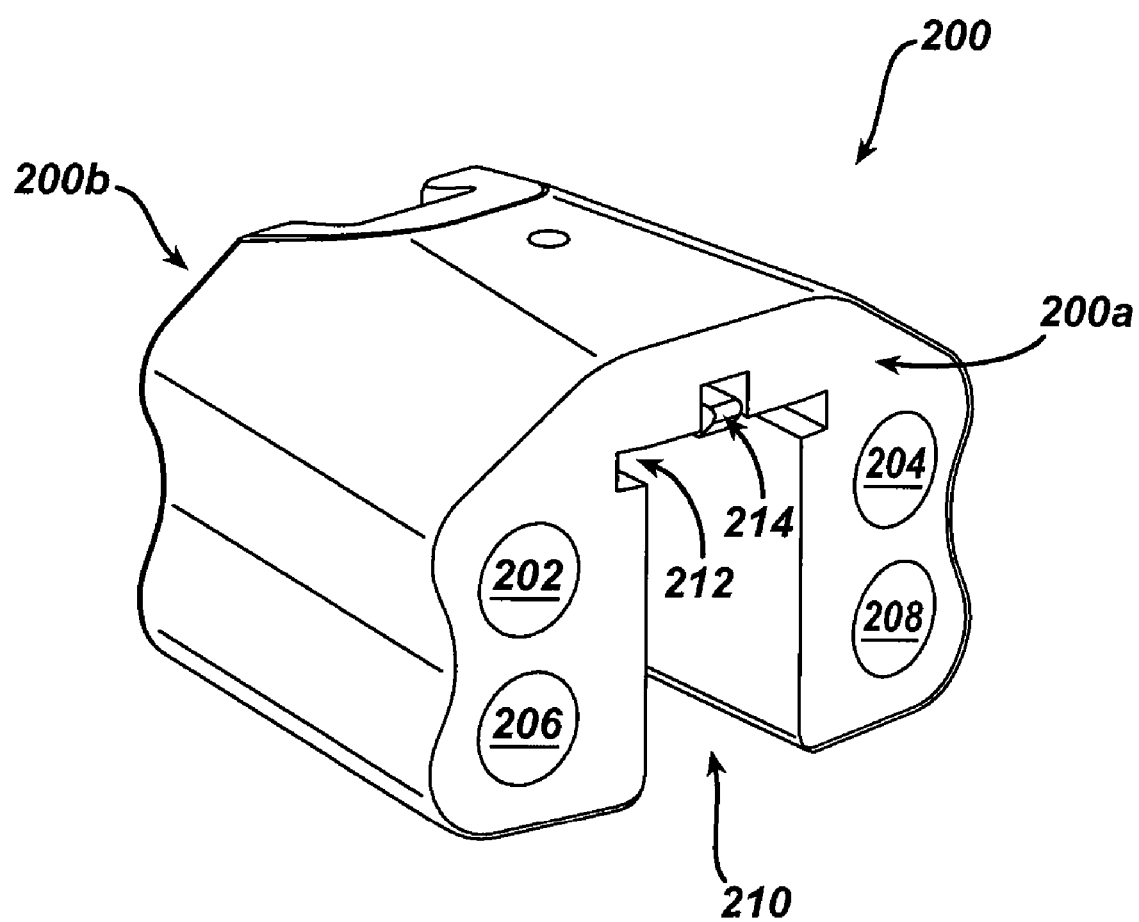
FIG. 3 is a proximal perspective view of a drill guide housing for use with the inserter tool shown in FIG. 2A.

In use, the inserter tool 100 can be configured to engage virtually any portion of a vertebra staple. However, in an exemplary embodiment, the inserter tool 100 is preferably configured to engage a substantial mid-portion of a staple. Referring to the staple 10 shown in FIGS. 1A-1D, the staple 10 is preferably substantially planar along the transverse axis T to facilitate engagement of the staple 10 by the inserter tool 100. The staple 10 can also include one ore more bores formed therein for receiving the hooks 116, 118. While the bores can be formed anywhere on the staple 10, in an exemplary embodiment the staple 10 includes first and second bores 24, 26 formed on opposed sides of the central spike 18 along the transverse axis T of the staple 10. The s In yet another embodiment of the present invention, the inserter tool 100 can be configured for use with a drill guide that is adapted to allow one or more tools to be inserted therethrough in alignment with one or more holes formed in a staple, such as holes 14, 16 formed in staple 10. FIG. 3 illustrates an exemplary embodiment of a drill guide 200 for use with the present invention. While the drill guide 200 is described in connection with staple 10, a person skilled in the art will appreciate that the drill guide 200 can be used with a variety of staples. As shown, the drill guide 200 is in the form of a generally elongate housing having opposed proximal and distal ends 200a, 200b. The housing can have virtually any shape, but as shown in FIG. 3 the housing has a generally rectangular or square shape, preferably with rounded edges extending between the proximal and distal ends 200a, 200b. The distal end 200a of the drill guide 200 is adapted to be positioned against the superior surface 12e of the staple 10, thus the distal end 200a preferably has a shape that is adapted to match the shape of the superior surface 12e of the staple 10. In particular, the distal end 200a of the drill guide 200 is preferably substantially concave such that is conforms to the curved shape of the staple 10. The shape can, of course, vary depending on the particular shape and configuration of the staple used in connection with the drill guide 200.

The drill guide 200 also includes at least one lumen extending therethrough for receiving a tool. While the guide 200 can include any number of lumens, FIG. 3 illustrates four lumens 202, 204, 206, 208 extending through the guide 200 between proximal and distal ends 200a, 200b thereof. The lumens 202, 204, 206, 208 are preferably positioned to align with one or more holes, such as holes 14, 16, formed in the staple 10. The lumens 202, 204, 206, 208 can also extend at a particular angle through the housing to serve as a trajectory guide for a tool being inserted therethrough.

In use, the drill guide 200 is preferably adapted to removably attach to inserter tool 100. Accordingly, the guide 200 and/or the inserter tool 100 can include one or more mating elements formed thereon to facilitate mating of the two devices 100, 200. While virtually any mating technique can be used, in an exemplary embodiment the drill guide 200 is configured to slidably receive the housing 112 on the distal end 102b of the elongate shaft 102. More particularly, the drill guide 200 can include a central opening or cavity 210 formed therein and extending therethrough for seating the housing 112. The cavity 210 should have a shape that conforms to the contour of the housing 112 to allow the housing 112 to be received therein. The cavity 210 can also include a T-shaped slot 212 formed therein and configured to receive a T-shaped member 115 formed on the housing 112, as shown in FIG. 2D. An engagement mechanism can optionally be provided to prevent the drill guide 200 from becoming disengaged with the inserter tool 100. By way of non-limiting example, FIG. 3 illustrates a leaf spring 214 that is disposed within the cavity 210 in the drill guide 200 and that is effective to be receive within a corresponding detent 117 formed in the housing 112. In use, the leaf spring 214 extends into and engages the detent 117 when the drill guide 200 is fully inserted over the inserter tool 100. The biasing connection can simply be overcome by pulling the two components 100, 200 apart from one another. A person skilled in the art will appreciate that a variety of other techniques can be used to removably mate the drill guide 200 to the inserter tool 100, and that the illustrated T-connection and leaf spring are merely one exemplary technique.

Figure 4:
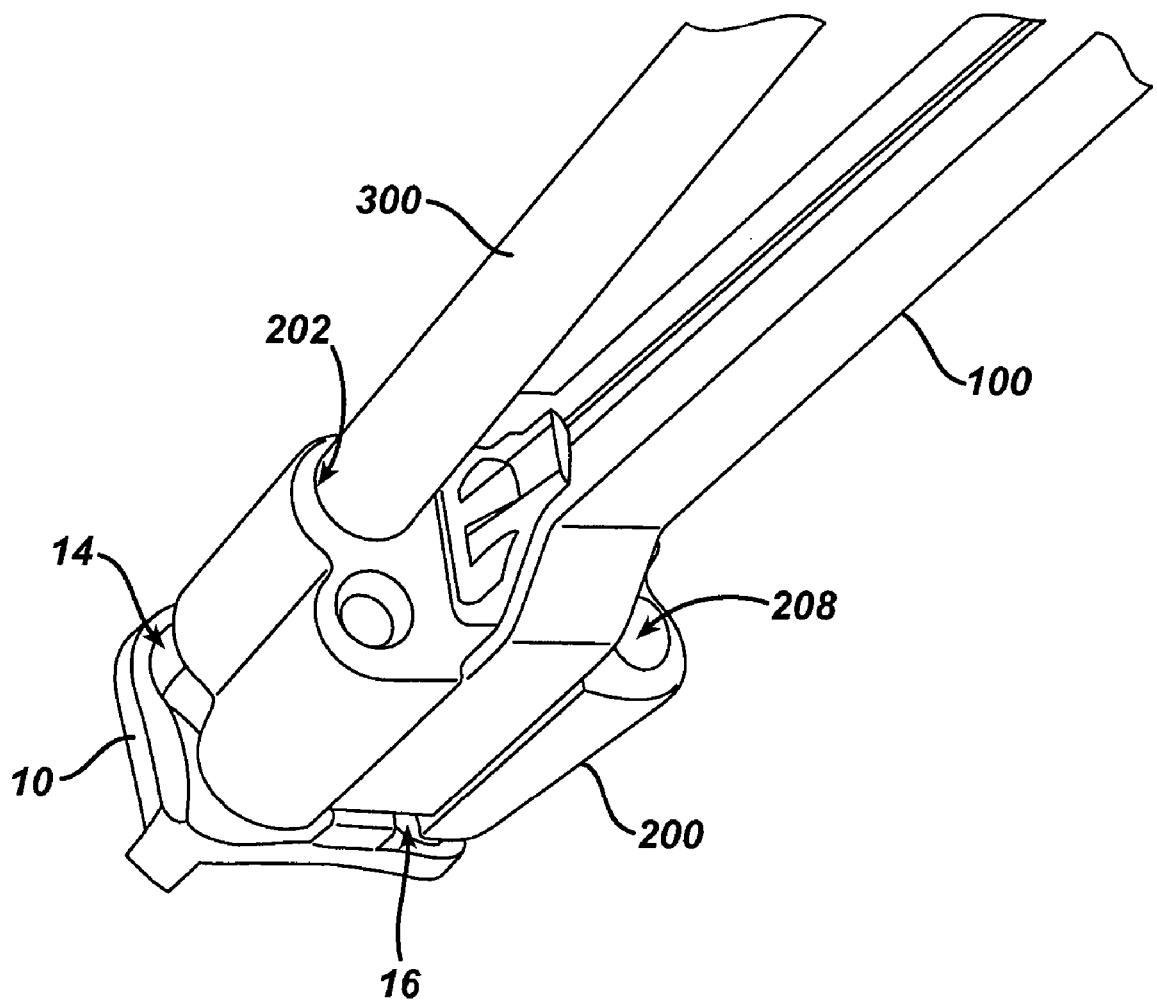
FIG. 4 is a perspective view of the vertebral staple shown in FIG. 1A engaged by the inserter tool shown in FIG. 2A having the drill guide shown in FIG. 3 disposed thereon and having an awl extending therethrough.

FIG. 4 illustrates the inserter tool 100 and drill guide 200 coupled to staple 10. As shown, the staple 10 is engaged by the staple-engaging member 106 of the inserter tool 100, and the drill guide 100 is passed over the inserter tool 100 such that the housing 112 on the distal end 102b of the elongate shaft 102 is received within the cavity 210 formed in the drill guide 100. Lumens 202 and 208 in the drill guide 100 are thus aligned with holes 14 and 16 in the staple, thereby allowing one or more tools to be inserted through the lumens 202, 208 and the holes 14, 16 to prepare the vertebra. As shown in FIG. 4, an awl 300 is passed through lumen 202 in the drill guide 200 and through hole 14 in the staple 10. Once the vertebra is prepared, the staple 10 can be released from the inserter tool 100 by rotating the actuating knob 114 to move the staple-engaging member 106 to the extended position, and then one or more screws can be inserted through the holes 14, 16 in the staple 10 to implant them in the vertebra. The screws can optionally be inserted through the drill guide 200 prior to removing the inserter tool 100 and drill guide 200 from the staple 10.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An implantable vertebral staple, comprising:
   a staple body having superior and inferior surfaces;
   first and second perimeter spikes formed on the staple body and formed adjacent to substantially diagonally opposed corners of the staple body;
   first and second holes formed in substantially diagonally opposed corners of the body opposite to the first and second perimeter spikes; and
   a central spike formed on the inferior surface of the staple body at a substantial mid-portion of the inferior surface of the staple body, the central spike being greater in length than any other spike on the inferior surface of the staple body such that the central spike can be partially inserted into bone without any other spike on the inferior surface of the staple body being inserted into bone to allow the staple body to rotate freely relative to the bone.

2. The implantable vertebral staple of claim 1, wherein the staple body is substantially rectangular in shape.

3. The implantable vertebral staple of claim 1, wherein the staple body has a shape adapted to match the contour of a surface of a vertebral body.

4. The implantable vertebral staple of claim 1, wherein the staple body has a shape adapted to match the contour of an anterior surface of a vertebral body.

5. The implantable vertebral staple of claim 1, wherein the staple body has a shape adapted to match the contour of a lateral surface of a vertebral body.

6. The implantable vertebral staple of claim 1, wherein the staple body includes proximal and distal ends with a longitudinal axis extending therebetween, and the staple body is curved about a transverse axis that intersects the longitudinal axis.

7. The implantable vertebral staple of claim 1, wherein a difference between the length of the central spike and a length of at least one of the first and second perimeter spikes is in the range of about 2 mm to 5 mm.

8. The implantable vertebral staple of claim 1, wherein the central spike has a sharp pointed tip adapted to penetrate bone.

9. The implantable vertebral staple of claim 1, wherein the at least one perimeter spike has a substantially triangular cross-sectional shape and a beveled tip.

10. The implantable vertebral staple of claim 1, further comprising first and second bores formed through the staple body for mating with an insertion tool.

11. The implantable vertebral staple of claim 10, wherein the first and second bores are formed on opposed sides of the central spike.

12. The implantable vertebral staple of claim 11, wherein the staple body includes a mid-portion that is substantially planar, and wherein the first and second bores are formed in the mid-portion.

* * * * *